(12) United States Patent
Jaehne et al.

(10) Patent No.: US 6,946,492 B2
(45) Date of Patent: Sep. 20, 2005

(54) USE OF C2-SUBSTITUTED INDAN-1-ONE SYSTEMS FOR PREPARING MEDICAMENTS FOR THE TREATMENT OF OBESITY

(75) Inventors: Gerhard Jaehne, Frankfurt (DE); Volker Krone, Hofheim (DE); Martin Bickel, Bad Homburg (DE); Matthias Gossel, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 316 days.

(21) Appl. No.: 10/231,162

(22) Filed: Aug. 30, 2002

(65) Prior Publication Data
US 2003/0134882 A1 Jul. 17, 2003

(30) Foreign Application Priority Data
Aug. 31, 2001 (DE) .......................................... 101 42 668

(51) Int. Cl.$^7$ ........................ A61K 31/12; A61K 31/13; A61K 31/095; A61K 31/41; A61K 31/38
(52) U.S. Cl. ........................ 514/681; 514/601; 514/613; 514/675; 514/681; 514/706; 514/381; 514/396; 514/383; 514/438; 514/461; 514/247; 514/374; 514/378; 514/372
(58) Field of Search ................................. 514/681, 601, 514/613, 675, 706, 381, 396, 383, 438, 461, 247, 374, 378, 372

(56) References Cited

FOREIGN PATENT DOCUMENTS

| EP | 0 009 554 | 4/1980 |
|----|-----------|--------|
| EP | 0 313 296 | 4/1989 |
| WO | WO97/20806 | 6/1997 |
| WO | WO97/26265 | 7/1997 |
| WO | WO97/41097 | 11/1997 |
| WO | WO98/08871 | 3/1998 |
| WO | WO99/03861 | 1/1999 |
| WO | WO00/51971 | 9/2000 |
| WO | WO01/02373 | 1/2001 |
| WO | WO01/12176 | 2/2001 |

OTHER PUBLICATIONS

C. Rufer et al., "Nichtsteroidale Entzündungshemmer. 8. (*) Entzündungshemmende Methansulfonanilide III.", Eur. J. Med. Chem.—Chem. Ther., vol. 8, No. 2, pp. 173–180, (1982).

D. Seebach, et al., "Herstellung α–Thiolierter Carbonylverbindungen", Chem. Ber., vol. 109, pp. 1601–1616, (1976).

H.J. Monteiro et al., "A New Synthesis of β–Keto–Phenylsulfoxides", Tetrahedron Letters, No. 11, pp. 921–924, (1975).

A. K. Maiti et al., "Polyethylene glycol (PEG) 4000 Catalysed Regioselective Nucleophilic Ring Opening of Oxiranes—A new and Convenient Synthesis of β–Hydroxy Sulfone and βHydroxy Sulfide", Tetrahedron, vol. 50, No. 35, pp. 10483–10490, (1994).

P. Tyle, "Iontophoretic Devices for Drug Delivery", Pharmaceutical Research, vol. 3, No. 6, pp. 318–326, (1986).

P.D. Lambert et al., "Ciliary Neurotrophic Factor Activates Leptin–Like Pathways and Reduces Body Fat, Without Cachexia or Rebound Weight Gain, Even in Leptin–Resistant Obesity", PNAS, vol. 98, No. 8, pp. 4652–4657, (Apr. 2001).

C.G. Venier et al., "Peroxytrifluoroacetic Acid. A Convenient Reagent for the Preparation of Sulfoxides and Sulfones", J. Org. Chem. vol. 47, pp. 3773–3774, (1982).

*Primary Examiner*—Sreeni Padmanabhan
*Assistant Examiner*—Jennifer Kim
(74) *Attorney, Agent, or Firm*—Balaram Gupta

(57) ABSTRACT

Embodiments of the invention relate to methods of reducing weight in mammals and for the prophylaxis or treatment of obesity comprising administration of C2-substituted indan-1-one systems and their physiologically acceptable salts and physiologically functional derivatives. Compounds for use in methods of embodiments of the invention may include compounds of the formula

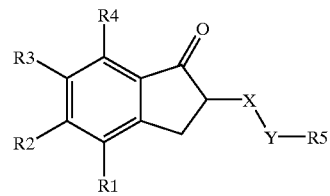

in which the radicals are as defined, and their physiologically acceptable salts.

16 Claims, No Drawings

USE OF C2-SUBSTITUTED INDAN-1-ONE SYSTEMS FOR PREPARING MEDICAMENTS FOR THE TREATMENT OF OBESITY

This application claims the benefit of foreign priority under 35 U.S.C. §119 of German patent application no. 10142668.2, filed on Aug. 31, 2001, the contents of which are expressly incorporated by reference herein.

DESCRIPTION

Use of C2-substituted indan-1-one systems for preparing medicaments for the prophylaxis or treatment of obesity.

Other applications that describe similar compounds and methods of using these compounds include: 1) "C2-substituted idan-1-ones and their derivatives, processes for their preparation and their use as pharmaceuticals" of Gerhard Jaehne, Volker Krone, Martin Bickel, and Matthias Gossel filed Aug. 31, 2002, "C2-substituted indan-1-ols and their derivatives, processes for their preparation and their use as pharmaceuticals" of Gerhard Jaehne, Volker Krone, Martin Bickel, and Matthias Gossel filed Aug. 31, 2002, and 3) "Use of C2-substituted indan-1-ol systems for preparing medicaments for the prophylaxis or treatment of obesity" of Gerhard Jaehne, Volker Krone, Martin Bickel, and Matthias Gossel filed Aug. 31, 2002,; all of which are hereby incorporated by reference.

Embodiments of the invention relate to the use of C2-substituted indan-1-one systems and their physiologically acceptable salts and physiologically functional derivatives, for preparing medicaments for reducing the weight of mammals and also for the prophylaxis or treatment of obesity.

EP 0009554 discloses indan-1-one and -1-ol derivatives as herbicides and analgesics.

EP 0313296 discloses indan-1-one and -1-ol derivatives as pharmaceuticals for asthma.

WO 97/20806 discloses cyclopentyl-substituted indan-1-one derivatives having inter alia antiinflammatory action.

In one embodiment, an object of the present invention is to provide compounds which can be used for reducing the weight of mammals and which have, in particular, a therapeutically utilizable anorectic action.

In accordance with an embodiment of the invention a method is provided for the prophylaxis or treatment of obesity comprising administering the compounds of the formula (I)

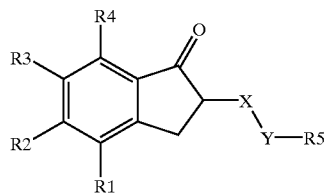

in which
R1, R2, R3, R4 independently of one another are H, F, Cl, Br, I, CN, $N_3$, $NO_2$, OH, $O(C_1$–$C_8)$-alkyl, $O(C_3$–$C_8)$-cycloalkyl, O—$CH_2$-phenyl, O-phenyl, O—CO—$(C_1$–$C_8)$-alkyl, O—CO—$(C_3$–$C_8)$-cycloalkyl, $S(O)_{0-2}$ $(C_1$–$C_8)$-alkyl, $S(O)_{0-2}(C_3$–$C_8)$-cycloalkyl, $NH_2$, NH—$(C_1$–$C_8)$-alkyl, NH—$(C_3$–$C_8)$-cycloalkyl, $N[(C_1$–$C_8)$-alkyl]$_2$, $N[(C_3$–$C_8)$-cycloalkyl]$_2$, NH—CO—$(C_1$–$C_8)$-alkyl, NH—CO—$(C_3$–$C_8)$-cycloalkyl, $SO_3H$, $SO_2$—$NH_2$, $SO_2$—NH—$(C_1$–$C_8)$-alkyl, $SO_2$—NH—$(C_3$–$C_8)$-cycloalkyl, NH—$SO_2$—$NH_2$, NH—$SO_2$—$(C_1$–$C_8)$-alkyl, NH—$SO_2$—$(C_3$–$C_8)$-cycloalkyl, O—$CH_2$—COOH, O—$CH_2$—CO—O$(C_1$–$C_8)$-alkyl, O—$CH_2$—COOH, O—$CH_2$—CO—O$(C_1$–$C_8)$-alkyl, COOH, CO—O $(C_1$–$C_8)$-alkyl, CO—O—$(C_3$–$C_8)$-cycloalkyl, CO—$NH_2$, CO—NH$(C_1$–$C_8)$-alkyl, CO—N$[(C_1$–$C_8)$-alkyl]$_2$, $(C_1$–$C_8)$-alkyl, $(C_3$–$C_8)$-cycloalkyl, $(C_2$–$C_8)$-alkenyl, or $(C_2$–$C_8)$-alkynyl, wherein the alkyl, cycloalkyl, alkenyl and alkynyl groups in each case have zero to seven hydrogen atoms replaced by fluorine, or one hydrogen may be replaced by OH, OC(O)$CH_3$, O—$CH_2$-Ph, $NH_2$, NH—CO—$CH_3$ or N(COOC$H_2$Ph)$_2$; or phenyl, 1- or 2-naphthyl,
5-tetrazolyl, 1-[$(C_1$–$C_6)$-alkyl]-5-tetrazolyl, 2-[$(C_1$–$C_6)$-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl,
3-, 4- or 5-isothiazolyl,
where the aryl radical or heterocycle is unsubstituted or substituted one to two times by F, Cl, Br, CN, OH, $(C_1$–$C_4)$-alkyl, $CF_3$, O—$(C_1$–$C_4)$-alkyl, $S(O)_{0-2}$ $(C_1$–$C_6)$-alkyl, $NH_2$, NH—$SO_2$—$(C_1$–$C_4)$-alkyl, COOH, CO—O—$(C_1$–$C_4)$-alkyl, or CO—$NH_2$, wherein the alkyl groups in each case have zero to seven hydrogen atoms replaced by fluorine; or R2 and R3 together form the group —O—$CH_2$—O—;
X is S, SO, or $SO_2$;
Y is $(CH_2)_p$, where p is 0, 1, 2 or 3;
R5 is $CF_3$, $(C_1$–$C_{18})$-alkyl, $(C_3$–$C_8)$-cycloalkyl, wherein the alkyl or cycloalkyl groups in each case have zero to seven hydrogen atoms replaced by fluorine;
$(CH_2)_r$—COR6, where r is 1–6 and R6 is OH, O—$(C_1$–$C_6)$-alkyl or $NH_2$;
$CH_2$—CH(NHR7)-COR8, where R7 is H, C(O)—$(C_1$–$C_4)$-alkyl or C(O)O—$(C_1$–$C_4)$-alkyl and R8 is OH, O—$(C_1$–$C_6)$-alkyl or $NH_2$; or
phenyl, 1- or 2-naphthyl, biphenyl or a heterocyclic radical, where the rings or ring systems are unsubstituted or substituted one or two times by F, Cl, Br, I, CN, OH, O$(C_1$–$C_8)$-alkyl, O$(C_3$–$C_8)$-cycloalkyl, O—CO—$(C_1$–$C_8)$-alkyl, O—CO—$(C_3$–$C_8)$-cycloalkyl, $S(O)_{0-2}$ $(C_1$–$C_8)$-alkyl, $S(O)_{0-2}(C_3$–$C_8)$-cycloalkyl, $NH_2$, NH—$(C_1$–$C_8)$-alkyl, NH—$(C_3$–$C_8)$-cycloalkyl, $N[(C_1$–$C_8)$-alkyl]$_2$, $N[(C_3$–$C_8)$-cycloalkyl]$_2$, NH—CO—$(C_2$–$C_8)$-alkyl, NH—CO—$(C_3$–$C_8)$-cycloalkyl, $SO_3H$, $SO_2$—$NH_2$, $SO_2$—NH—$(C_1$–$C_8)$-alkyl, $SO_2$—NH—$(C_3$–$C_8)$-cycloalkyl, NH—$SO_2$—$NH_2$, NH—$SO_2$—$(C_1$–$C_8)$-alkyl, NH—$SO_2$—$(C_3$–$C_8)$-cycloalkyl, O—$CH_2$—COOH, O—$CH_2$—CO—O$(C_1$–$C_8)$-alkyl, COOH, CO—O$(C_1$–$C_8)$-alkyl, CO—O—$(C_3$–$C_8)$-cycloalkyl, CO—$NH_2$, CO—NH$(C_1$–$C_8)$-alkyl, CO—N$[(C_1$–$C_8)$-alkyl]$_2$, $(C_1$–$C_8)$-alkyl, or $(C_3$–$C_8)$-cycloalkly, where in the alkyl and cycloalkyl groups in each case have zero to seven hydrogen atoms replaced by fluorine; or
F, Cl, Br, I, or CN;
and their physiologically acceptable salts.

In one embodiment, compounds of the formula I for use in the methods of the invention are chosen from compounds of the formula I in which R1, R4 independently of one another are H, F, Cl, Br, I, CN, $N_3$, $NO_2$, OH, $O(C_1-C_8)$-alkyl, $O(C_3-C_4$ and $C_6-C_8)$-cycloalkyl, $O-CH_2$-phenyl, O-phenyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl$]_2$, $N[(C_3-C_8$-cycloalkyl$)]_2$, $NH-CO-(C_1-C_8)$-alkyl, $NH-CO-(C_3-C_8)$-cycloalkyl, $SO_3H$, $SO_2-NH_2$, $SO_2-NH-(C_1-C_8)$-alkyl, $SO_2-NH-(C_3-C_8)$-cycloalkyl, $NH-SO_2-NH_2$, $NH-SO_2-(C_1-C_8)$-alkyl, $NH-SO_2-(C_3-C_8)$-cycloalkyl, $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl$]_2$, $(C_1-C_8)$-alkyl, $(C_3-C_8)$-cycloalkyl, $(C_2-C_8)$-alkenyl, $(C_2-C_8)$-alkynyl, where in the alkyl, cycloalkyl, alkenyl and alkynyl groups in each case have zero to seven hydrogen atoms replaced by fluorine, or one hydrogen may be replaced by OH, $OC(O)CH_3$, $O-CH_2-Ph$, $NH_2$, $NH-CO-CH_3$ or $N(COOCH_2Ph)_2$; or phenyl, 1- or 2-naphthyl, 5-tetrazolyl, 1-$[(C_1-C_6)$-alkyl]-5-tetrazolyl, 2-$[(C_1-C_6)$-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, 3-, 4- or 5-isothiazolyl where the aryl radical or heterocycle are unsubstituted or substituted one or two times by F, Cl, Br, CN, OH, $(C_1-C_4)$-alkyl, $CF_3$, $O-(C_1-C_4)$-alkyl, $S(O)_{0-2}(C_1-C_6)$-alkyl, $NH_2$, $NH-SO_2-(C_1-C_4)$-alkyl, COOH, $CO-O-(C_1-C_4)$-alkyl, or $CO-NH_2$ wherein the alkyl groups in each case have zero to seven hydrogen atoms replaced by fluorine;

R2, R3 independently of one another are H, F, Cl, Br, I, CN, $N_3$, $NO_2$, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_1-C_8)$-alkyl, $NH-CO-(C_3-C_8)$-cycloalkyl, $SO_3H$, $SO_2-NH_2$, $SO_2-NH-(C_5-C_8)$-alkyl, $SO_2-NH-(C_3-C_8)$-cycloalkyl, $NH-SO_2-NH_2$, $NH-SO_2-(C_1-C_8)$-alkyl, $NH-SO_2-(C_5-C_8)$-cycloalkyl, $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl$]_2$, $(C_1-C_8)$-alkyl, $(C_3-C_8)$-cycloalkyl, $(C_2-C_8)$-alkenyl, or $(C_2-C_8)$-alkynyl, where in the alkyl, cycloalkyl, alkenyl and alkynyl groups in each case have zero to seven hydrogen atoms replaced by fluorine, or one hydrogen may be replaced by OH, $OC(O)CH_3$, $O-CH_2-Ph$, $NH_2$, $NH-CO-CH_3$ or $N(COOCH_2Ph)_2$; or phenyl, 1- or 2-naphthyl, 5-tetrazolyl, 1-$[(C_1-C_6)$-alkyl]-5-tetrazolyl, 2-$[(C_1-C_6)$-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, 3-, 4- or 5-isothiazolyl where the heterocycle is unsubstituted or substituted one or two times by F, Cl, Br, CN, OH, $(C_1-C_4)$-alkyl, $CF_3$, $O-(C_1-C_4)$-alkyl, $S(O)_{0-2}(C_1-C_6)$-alkyl, $NH_2$, $NH-SO_2-(C_1-C_4)$-alkyl, COOH, $CO-O-(C_1-C_4)$-alkyl, or $CO-NH_2$ and in the alkyl groups in each case have zero to seven hydrogen atoms replaced by fluorine;

or R2 and R3 together form the group $-O-CH_2-O-$;

where in each case at least one of the radicals R1, R2, R3 and R4 is different from hydrogen;

X is S, SO, or $SO_2$;

Y is $(CH_2)_p$, where p is 0, 1, 2 or 3;

R5 is $(C_1-C_{18})$-alkyl, or $(C_3-C_4$- and $C_6-C_8)$-cycloalkyl, wherein the alkyl or cycloalkyl groups in each case have zero to seven hydrogen atoms replaced by fluorine;

$(CH_2)_r$-COR6, where r is 1–6 and R6 is OH, $O-(C_1-C_6)$-alkyl or $NH_2$;

$CH_2-CH(NHR7)$-COR8, where R7 is H, $C(O)-(C_1-C_4)$-alkyl or $C(O)O-(C_1-C_4)$-alkyl and R8 is OH, $O-(C_1-C_6)$-alkyl or $NH_2$;

phenyl, 1- or 2-naphthyl, biphenyl or a heterocyclic radical, where the rings or ring systems are unsubstituted or substituted up to two times by $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl$]_2$, $N[(C_3-C_8)$-cycloalkyl$]_2$, $NH-CO-(C_2-C_8)$-alkyl, $NH-CO-(C_3-C_8)$-cycloalkyl, $SO_3H$, $SO_2-NH_2$, $SO_2-NH-(C_1-C_8)$-alkyl, $SO_2-NH-(C_3-C_8)$-cycloalkyl, $NH-SO_2-NH_2$, $NH-SO_2-(C_1-C_8)$-alkyl, $NH-SO_2-(C_3-C_8)$-cycloalkyl, $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl$]_2$, $(C_1-C_8)$-alkyl, $(C_3-C_8)$-cycloalkyl, where in the alkyl and cycloalkyl groups in each case have zero to seven hydrogen atoms replaced by fluorine; or F, Cl, Br, I, or CN;

and their physiologically acceptable salts.

In another embodiment, compounds of the formula I for use in the methods of the invention are chosen from compounds of the formula I in which R1, R4 independently of one another are H, F, Cl, or Br;

R2, R3 independently of one another are H, F, Cl, Br, CN, $CONH_2$, $NH-SO_2-(C_1-C_8)$-alkyl, $O-(C_1-C_8)$-alkyl, COOH, $(C_1-C_8)$-alkyl, $(C_1-C_8)$-alkenyl, or $(C_1-C_8)$-alkynyl, where in the alkyl, alkenyl and alkynyl groups in each case have zero to seven hydrogen atoms replaced by fluorine; or phenyl, or 1-imidazolyl, where the rings may be substituted up to two times by F, Cl, Br, CN, OH, $(C_1-C_4)$-alkyl, or $CF_3$, $O-(C_1-C_4)$-alkyl, wherein the alkyl groups in each case have zero to seven hydrogen atoms may be replaced by fluorine;
where in each case at least one of the radicals R1, R2, R3 and R4 is different from hydrogen;
X is S or $SO_2$;
Y is $(CH_2)_p$, where p is 0 or 1;
R5 is $(C_1–C_{18})$-alkyl or $(C_3–C_4$- and $C_6–C_8)$-cycloalkyl, wherein the alkyl or cycloalkyl groups have zero to seven hydrogen atoms replaced by fluorine;
$(CH_2)_r$—CO—O—$(C_1–C_6)$-alkyl, where r is 1–6;
$CH_2$—CH(NHR7)-COR8, where R7 is H, C(O)—$(C_1–C_4)$-alkyl or C(O)O—$(C_1–C_4)$-alkyl and R8 is OH, O—$(C_1–C_6)$-alkyl or $NH_2$;
phenyl, or a heterocyclic radical;
and their physiologically acceptable salts.

In one embodiment, the invention relates to compounds of the formula I in the form of their racemates, racemic mixtures and pure enantiomers, and also to their diastereomers and mixtures thereof. As used herein, any stereoisomeric form includes racemates, racemic mixtures and pure enantiomers, and also to their diastereomers and mixtures thereof.

As used herein, alkyl, alkenyl and alkynyl radicals in the substituents R1, R2, R3, R4, R5, R6, R7 and R8 can be straight-chain or branched.

Heterocycle or heterocyclic radical is to be understood as meaning ring systems which, in addition to carbon, also contain heteroatoms, such as, for example, nitrogen, oxygen or sulfur. This definition furthermore includes ring systems in which the heterocycle or heterocyclic radical is fused with benzene rings. Example of heterocycles or heterocyclic radicals include, but are not limited to:

heteroaryls, such as
benzimidazolyl,
1-[$(C_1–C_6)$-alkyl]benzimidazolyl,
imidazolyl,
2- or 3-thienyl,
2- or 3-furyl,
benzoxazolyl,
benzothiazolyl,
2-, 3- or 4-pyridyl,
pyrimidinyl,
4-, 5- or 6-pyridazin-2H-yl-3-one,
4-, 5- or 6-pyridazin-2-$(C_1–C_8)$-alkyl-2H-yl-3-one,
2-benzyl-4-, -5- or -6-pyridazin-2H-yl-3-one,
3- or 4-pyridazinyl,
2-, 3-, 4- or 8-quinolinyl,
1-, 3- or 4-isoquinolinyl,
1-phthalazinyl,
3- or 4-cinnolinyl,
2- or 4-quinazolinyl,
2-pyrazinyl,
2-quinoxalinyl,
2-, 4- or 5-oxazolyl,
3-, 4- or 5-isoxazolyl,
2-, 4- or 5-thiazolyl,
3-, 4- or 5-isothiazolyl,
1-[$(C_1–C_6)$-alkyl]-2-, -4- or -5-imidazolyl,
3-, 4- or 5-pyrazolyl,
1-[$(C_1–C_6)$-alkyl]-3-, -4- or -5-pyrazolyl,
1- or 4-[1,2,4]triazolyl,
4- or 5-[1,2,3]triazolyl,
1-[$(C_1–C_6)$-alkyl]-4- or -5-[1,2,3]triazolyl,
3-, 4- or 7-indolyl,
N[$(C_1–C_6)$-alkyl]-3-, -4- or -7-indolyl
2-[$(C_1–C_6)$-alkyl]-3(2H)-indazolyl,
1-[$(C_1–C_6)$-alkyl]-3(1H)-indazolyl,
5-tetrazolyl,
1-[$(C_1–C_6)$-alkyl]-1H-tetrazolyl,
2-[$(C_1–C_6)$-alkyl]-2H-tetrazolyl.

Pharmaceutically acceptable salts are particularly suitable for medical applications, due to their greater solubility in water compared with the starting or base compounds. Said salts must have a pharmaceutically acceptable anion or cation. Suitable pharmaceutically acceptable acid addition salts of the compounds of the invention include salts of inorganic acids such as hydrochloric acid, hydrobromic acid, phosphoric acid, metaphosphoric acid, nitric acid and sulfuric acid and also of organic acids such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methane-sulfonic acid, succinic acid, p-toluenesulfonic acid, tartaric acid and trifluoroacetic acid, furthermore L-ascorbic acid, salicylic acid, 1,2-benzisothiazol-3(2H)-one and 6-methyl-1,2,3-oxathiazin-4(3H)-one 2,2-dioxide. For some medicinal purposes, particular preference may be given to using the chlorine salt. Examples of suitable pharmaceutically acceptable basic salts are ammonium salts, alkali metal salts (such as sodium salts and potassium salts) and alkaline earth metal salts (such as magnesium salts and calcium salts).

In one embodiment, salts having a pharmaceutically unacceptable anion are likewise included within the scope of the present invention, for example, as useful intermediates for preparing or purifying pharmaceutically acceptable salts and/or for use in nontherapeutic applications, such as in-vitro applications.

As used herein, treating or treatment includes the treating of, for example, a patient inflicted with a disease or condition, as well as the prevention, prophylaxis, or protective treatment of a patient. Thus, for example, treatment of obesity includes reducing and/or maintaining the weight of a subject who is inflicted with obesity or is susceptible to obesity. The treatment of obesity also includes inhibiting and/or slowing the weight gain of a subject who is inflicted with obesity or is susceptible to obesity. Treatment of obesity also includes treating a subject susceptible to or predisposed to developing obesity, which could include patients in whom obesity has not yet presented as well as patients in whom the disease has been successfully treated but could redevelop or reoccur.

As used herein controlling weight includes reducing and/or maintaining the weight of a subject. Controlling weight also includes inhibiting and/or slowing the weight gain of a subject. Thus, for example, the phrase weight controlling compounds includes weight-reducing compounds.

The term "physiologically functional derivative" used herein relates to any physiologically acceptable derivative of an inventive compound, for example an ester which on administration to a mammal, for example humans, is capable of forming (directly or indirectly) such a compound or an active metabolite thereof.

The physiologically functional derivatives also include prodrugs of the compounds of the invention. Such prodrugs may be metabolized in vivo to a compound of the invention. These prodrugs may or may not be active themselves.

The physiologically functional derivatives furthermore include, for example, derivatives derived from sugars, such as, glycosides and ribosides, glucuronides, and sulfuric acid esters.

The compounds of the formula I may also be present in various polymorphous forms, for example as amorphous and crystalline polymorphous forms. All polymorphous forms of the compounds of the formula I are included within the scope of the invention.

All references to compound(s) of the formula (I) herein refer to a compound/compounds of the formula (I) as described herein and also to their solvates, physiologically functional derivatives, and polymorphs as described herein.

In one embodiment, the amount of a compound according to formula (I) used to attain a desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3–10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampules for injections can contain, for example, from 1 mg to 100 mg, and orally administerable individual dose formulations such as, for example, tablets or capsules can contain, for example, from 1.0 to 1000 mg, typically from 10 to 600 mg. In one embodiment, the use of a compound of formula (I) as a prophylaxis may require a lower amount of a compound of formula (I), but still within the range disclosed above, for the patient of interest.

In the case of pharmaceutically acceptable salts, the abovementioned masses relate to the mass of the free base or acid on which the salt is based. The compound used for the prophylaxis or therapy of the abovementioned conditions may be the compounds according to formula (I) themselves, or, in one embodiment, they are present in the form of a pharmaceutical composition together with an acceptable carrier. In one embodiment, the carrier must be naturally acceptable, in the sense that it is compatible with the other ingredients of said composition and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. In one embodiment, preference is given to acid-resistant and enteric formulations. Suitable enteric coatings include, for example, cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be present in separate units as, for example, capsules, cachets, lozenges or tablets, which in each case contain a particular amount of the compound according to formula (I); as powders or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine.

Pharmaceutical compositions which are suitable for peroral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration may, for example, comprise sterile aqueous preparations of a compound according to formula (I) which are isotonic with the blood of the intended recipient. These preparations may be administered intravenously, although they may also be administered subcutaneously, intramuscularly or intradermally as an injection. Said preparations may be prepared by mixing the compound with water and rendering the obtained solution sterile and isotonic with the blood. Injectable compositions of the invention generally contain from 0.1 to 5% by weight of the active compound.

Suitable pharmaceutical compositions for rectal administration may be present as individual dose suppositories. These may be prepared by mixing a compound according to formula (I) with one or more conventional solid carriers, for example cocoa butter, and shaping the resulting mixture.

Suitable pharmaceutical compositions for topical application to the skin may be present as ointment, cream, lotion, paste, spray, aerosol or oil. Carriers which may be used are petroleum jelly, lanolin, polyethylene glycols, alcohols and combinations of two or more of these substances. In one embodiment, the active compound is present at a concentration ranging from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration in one embodiment ranges from approx. 1% to 35%, such as approx. 3% to 15%. A particular possibility is the release of the active compound by electrotransport or iontophoresis, as described, for example, in Pharmaceutical Research, 2(6): 318 (1986).

The invention furthermore provides a process for preparing the compounds of the formula I which comprises preparing compounds of the formula I by proceeding according to the reaction schemes below:

Compounds of the formula I in which X=SO can be prepared, for example, by selective oxidation of the compound of the formula I in which X=S, using one equivalent of peroxytrifluoroacetic acid (C. G. Venier et al.; J. Org. Chem. 47, 3773 (1982)). The preparation of the sulfoxides from the sulfides can also be carried out using manganese dioxide or chromic acid (D. Edwards et al.; J. Chem. Soc. 1954, 3272). Furthermore suitable for this oxidation is hydrogen peroxide in acetic anhydride (A. V. Sviridova et al.; J. Org. Chem (Russ), English Transl.; 7, 2577 (1971)).

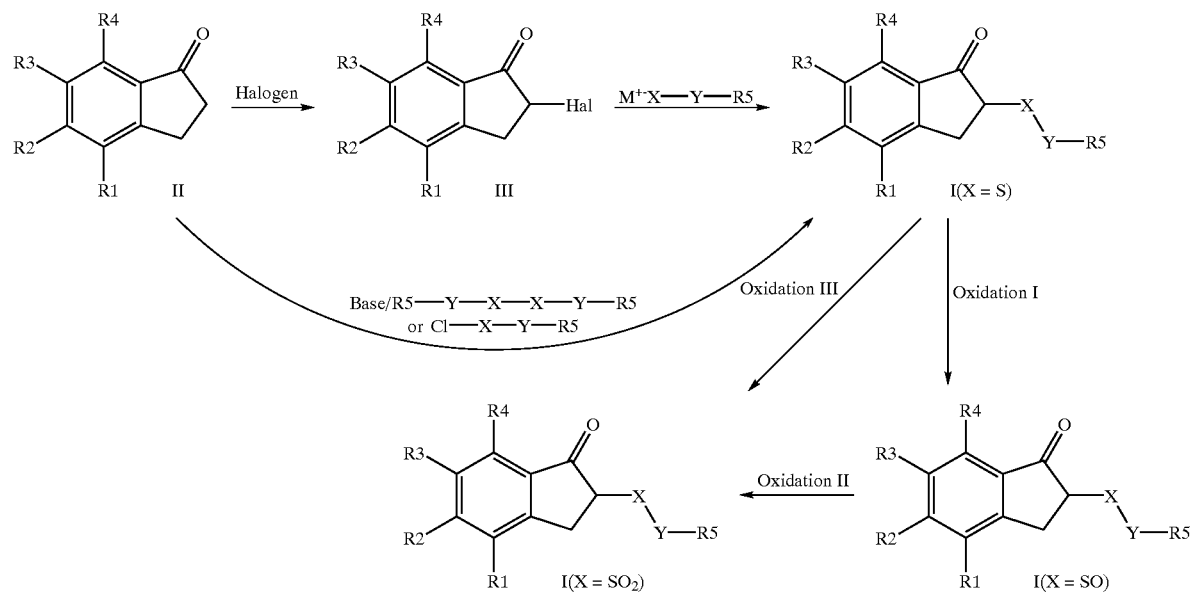

To this end, compounds of the formula II,

Formula II

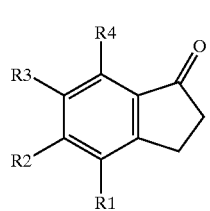

in which R1, R2, R3 and R4 are as defined above are converted with a halogen, such as, for example, bromine or chlorine, into a compound of the formula III. The compounds of the formula III are converted further with metal salts of thiols of the formula H—X—Y—R5, where X is sulfur and Y and R5 are as defined above into compounds of the formula I where X=S. These metal salts can be employed as such or they can be generated in solution in situ from the thiol and a base, such as, for example, aqueous sodium hydroxide. On the other hand, in another embodiment, compounds of the formula I where X=S can be obtained by reacting compounds of the formula 11 with a base, such as, for example, lithium diisopropylamide, for example in tetrahydrofuran, and with a disulfide of the formula R5-Y—X—X—Y—R5 in which R5 and Y are as defined above and X=S. Alternatively, instead of the disulfide, it is also possible to use a sulfenyl chloride of the formula Cl—X—Y—R5 where X=S and Y and R5 are as defined above (see, for example, D. Seebach et al.; Chem. Ber. 109, 1601–1616 (1976)).

Compounds of the formula I in which X=$SO_2$ can be obtained by oxidation using, for example, 2$KHSO_5$x$KHSO_4$x$K_2SO_4$ (Oxone), either from compounds of the formula I in which X=S or from compounds of the formula I in which X=SO (see, for example, M. Hudlický, Oxidations in Organic Chemistry, ACS Monograph 186, American Chemical Society, Washington, D.C., 1990).

Compounds of the formula I in which X=SO or $SO_2$ and Y=a bond (=($CH_2$)m where m=0) can also, alternatively, be prepared according to the scheme below (shown for the preparation of the aryl sulfoxides (H. J. Monteiro et al.; Tetrahedron Letters 11, 921–924 (1975) and aryl sulfones (A. K. Maiti et al.; Tetrahedron 50, 10483–10490 (1994)):

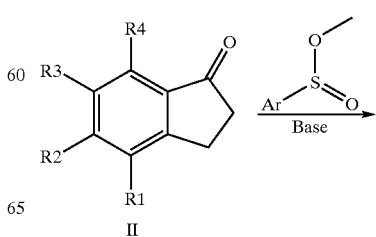

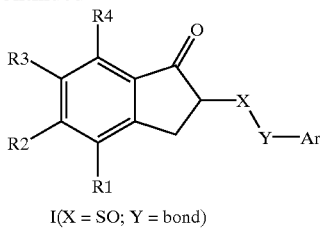

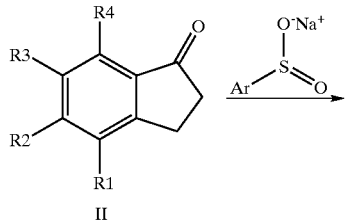

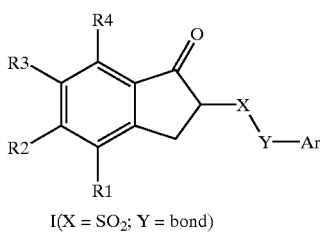

Inorganic acids suitable for forming salts are, for example: hydrohalic acids, such as hydrochloric acid and hydrobromic acid, and also sulfuric acid, phosphoric acid and amidosulfonic acid.

Organic acids suitable for salt formation which may be mentioned are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide.

The examples shown below serve to illustrate the invention without limiting it. The melting points or decomposition points (m.p.) measured are uncorrected and generally depend on the heating rate.

The retention times given in the table below refer to the following methods for determination:

Method A: Column: Merck, LiChroCart 55-2, PuroSpher STAR, RP 18 e; measured at 254 nm; gradient: solvent A acetonitrile/water 90:10+0.5% formic acid; solvent B acetonitrile/water 10:90+0.5% formic acid; flow rate: 0.750 ml/min; time (min)/solvent B (%): 0.00/95.0, 0.50/95.0, 1.75/5.0, 4.25/5.0, 4.50/95.0, 5.00/95.0; temperature: 40° C.:

Method B: column: YMC J'sphere, 33×2, ODS H 80 4µ; measured at 254 nm; gradient: solvent A acetonitrile+0.5% formic acid; solvent B water+0.5% formic acid; flow rate: 1.00 ml/min; time (min)/solvent B (%): 0.00/90.0, 2.50/5.0, 3.30/5.0, 3.35/90.0; temperature: 30° C.:

TABLE 1

Examples

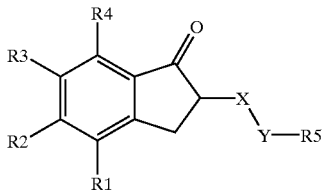

Formula I

| Example | R1 | R2 | R3 | R4 | X | Y | R5 | m.p. [° C.] |
|---|---|---|---|---|---|---|---|---|
| 1 | H | Cl | H | H | S | — | $CH_3$ | 90 |
| 2 | H | Cl | H | H | $SO_2$ | — | $CH_3$ | 196 |
| 3 | H | Cl | H | H | S | — | $C_6H_5$ | 89 |
| 4 | H | Cl | H | H | $SO_2$ | — | $C_6H_5$ | 133 [MH$^+$] |
| 5 | Br | $OCH_3$ | H | H | $SO_2$ | — | $CH_3$ | 319.1/ 321.1 |
| 6 | H | thien-3-yl | H | H | $SO_2$ | — | $CH_3$ | 293.2 |
| 7 | H | HCC | H | H | $SO_2$ | — | $CH_3$ | 235.1 |
| 8 | H | HOOC | H | H | $SO_2$ | — | $CH_3$ | 255.2 |
| 9 | H | Cl | H | H | SO | — | $CH_3$ | 228.87 Retention time in min (method A or B) |
| 10 | H | $C_6H_4$-4-Cl | H | H | $SO_2$ | — | $CH_3$ | 2.834 (A) |
| 11 | H | $CF_3$ | H | H | $SO_2$ | — | $CH_3$ | 2.695 (A) |
| 12 | H | Cl | H | H | S | — | $CH_2CH(COOCH_3)(NH$—$COO$—$C(CH_3)_3)$ | 2.903 (A) |

TABLE 1-continued

Examples

Formula I

| Example | R1 | R2 | R3 | R4 | X | Y | R5 | m.p. [° C.] |
|---|---|---|---|---|---|---|---|---|
| 13 | H | Cl | H | H | S | — | $CH_2CH(COOH)(NH-COO-C(CH_3)_3)$ | 2.787 (A) |
| 14 | H | Cl | H | H | S | — | $CH_2CH(COOCH_3)(NH\,COCH_3)$ | 2.675 (A) |
| 15 | H | Cl | H | H | S | — | $CH_2CH(COOH)(NH-COCH_3$ | 2.584 (A) |
| 16 | H | Cl | H | H | S | — | $CH_2-CH_2-CH_3$ | 2.715 (B) |
| 17 | H | Cl | H | H | S | — | $CH_2-CF_3$ | 2.993 (A) |
| 18 | H | Cl | H | H | S | — | $CH_2-COOCH_3$ | 2.835 (A) |
| 19 | H | Cl | H | H | S | $CH_2$ | $C_6H_5$ | 3.135 (A) |
| 20 | H | Cl | H | H | S | — | cyclohexyl | 3.288 (A) |
| 21 | H | Cl | H | H | S | — | pyrimidin-2-yl | 2.806 (A) |
| 22 | H | Cl | H | H | S | — | pyridin-2-yl | 2.976 (A) |
| 23 | H | Cl | H | H | S | — | cyclopentyl | 3.023 (B) |
| 24 | H | Cl | H | H | S | $CH_2$ | pentyl | 3.163 (B) |
| 25 | H | $CONH_2$ | H | H | S | $CH_2$ | nonyl | 3.283 (A) |
| 27 | H | H | H | H | S | — | benzoxazol-2-yl | 2.949 (A) |
| 28 | H | H | $C_6H_4$-4-$CF_3$ | H | S | $CH_2$ | $C_6H_5$ | 3.397 (A) |
| 29 | H | H | $C_6H_4$-4-$CF_3$ | H | $SO_2$ | — | $CH_3$ | 2.503 (B) |
| 30 | Br | H | H | H | $SO_2$ | — | $CH_3$ | 1.927 (B) |
| 31 | H | H | $C_6H_4$-4-$CF_3$ | H | S | — | $CH(CH_3)_2$ | 3.069 (B) |
| 32 | H | H | $C_6H_5$ | H | S | — | cyclopentyl | 3.078 (B) |
| 33 | H | $NHSO_2CH_3$ | H | H | S | — | $C(CH_3)_2-CH(COOH)(NHCOCH_3)$ | 1.637 (B) |
| 34 | H | N-phthalimi-doyl | H | H | $SO_2$ | — | $CH_3$ | 2.665 (A) |
| 35 | H | $OCH_3$ | H | H | $SO_2$ | — | $CH_3$ | 1.671 (B) |
| 36 | H | OH | H | H | S | $CH_2$ | $C_6H_5$ | 2.279 (B) |
| 37 | H | Cl | H | H | $SO_2$ | $CH_2$ | $CH(COOCH_3)(NH-COO-C(CH_3)_3)$ | 1.565 (B) |
| 38 | H | Cl | H | H | $SO_2$ | $CH_2$ | $CH(COOH)(NH-COO-C(CH_3)_3)$ | 1.399 (B) |
| 39 | H | Cl | H | H | $SO_2$ | $CH_2$ | $CH(COOCH_3)(NHCO\,CH_3)$ | 1.137 (B) |
| 40 | H | Cl | H | H | $SO_2$ | $CH_2$ | $CH(COOH)(NH-COCH_3$ | 1.011 (B) |
| 41 | H | Cl | H | H | $SO_2$ | $CH_2$ | $CH_2-CH_3$ | 1.393 (B) |
| 42 | H | Cl | H | H | $SO_2$ | $CH_2$ | $CF_3$ | 1.523 (B) |
| 43 | H | Cl | H | H | $SO_2$ | $CH_2$ | $COOCH_3$ | 1.342 (B) |
| 44 | H | Cl | H | H | $SO_2$ | $CH_2$ | $C_6H_5$ | 1.577 (B) |

TABLE 1-continued

Examples

Formula I

| Example | R1 | R2 | R3 | R4 | X | Y | R5 | m.p. [° C.] |
|---|---|---|---|---|---|---|---|---|
| 45 | H | Cl | H | H | SO$_2$ | — | pyrimidin-2-yl | 1.205 (B) |
| 46 | H | Cl | H | H | SO$_2$ | — | pyridin-2-yl | 1.325 (B) |
| 47 | H | Cl | H | H | SO$_2$ | — | cyclopentyl | 1.617 (B) |
| 48 | H | Cl | H | H | SO$_2$ | CH$_2$ | pentyl | 1.765 (B) |
| 49 | H | Cl | H | H | SO$_2$ | CH$_2$ | CH2—C$_6$H$_5$ | 1.663 (B) |
| 50 | H | CN | H | H | SO$_2$ | CH$_2$ | pentyl | 1.621 (B) |
| 51 | H | H | C$_6$H$_5$ | H | SO$_2$ | — | cyclopentyl | 1.716 (B) |
| 52 | H | OH | H | H | SO$_2$ | CH$_2$ | C$_6$H$_5$ | 1.311 (B) |
| 53 | H | Cl | H | H | SO$_2$ | CH$_2$ | CH(NH$_2$)(COOCH$_3$) | 1.993 (B) |
| 54 | H | Cl | H | H | S | CH$_2$ | CH(NH$_2$)(COOH) | 2.174 (B) |

In one embodiment, the compounds of the formula I are distinguished by beneficial actions on the metabolism of lipids, and they are particularly suitable for weight reduction and, after weight reduction, for maintaining a reduced weight in mammals and as anorectic agents. The compounds are distinguished by their low toxicity and their few side effects. The compounds may be employed alone or in combination with other weight-reducing or anorectic active compounds. Further anorectic active compounds of this kind are mentioned, for example, in the Rote Liste, Chapter 01 under weight-reducing agents/appetite suppressants, herein incorporated by reference, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The compounds may be suitable for controlling or the prophylaxis and, in particular, for the treatment of problems of excess weight or obesity. The compounds may furthermore be suitable for the prophylaxis and, in particular, for the treatment of type II diabetes, of arteriosclerosis and for the normalization of lipid metabolism and for the treatment of high blood pressure.

In a further aspect of the invention, the compounds of the formula I may be administered in combination with one or more further pharmacologically active substances which may be selected, for example, from the group consisting of antidiabetics, antiadipose agents, blood-pressure-lowering active compounds, lipid reducers and active compounds for the treatment and/or prevention of complications caused by diabetes or associated with diabetes. One of skill in the art, based on the activity and the known amounts for administration of the above compounds, will be able to readily determine the amounts of these compounds that are useful in a combination therapy with the compounds of the invention.

Suitable antidiabetics include insulins, amylin, GLP-1 and GLP-2 derivatives such as, for example, those disclosed by Novo Nordisk A/S in WO 98/08871 and also oral hypoglycemic active compounds.

In one embodiment, said oral hypoglycemic active compounds include sulfonyl ureas, biguamides, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor kinase, inhibitors of liver enzymes involved in the stimulation of gluconeogenesis and/or glycogenolysis, for example glycogen phosphorylase inhibitors, modulators of glucose uptake and glucose elimination, lipid metabolism-modifying compounds such as antihyperlipidemic active compounds and antilipidemic active compounds, for example HMGCoA-reductase inhibitors, inhibitors of cholesterol transport/cholesterol uptake, inhibitors of the reabsorption of bile acid or inhibitors of microsomal triglyceride transfer protein (MTP), compounds which reduce food intake, PPAR and RXR agonists and active compounds which act on the ATP-dependent potassium channel of beta cells.

In one embodiment of the present invention, the present compounds are administered in combination with insulin.

In another embodiment, the compounds of the invention are administered in combination with a sulfonylurea such as, for example, tolbutamide, glibenclamide, glimepiride, glipizide, gliquidone, glisoxepide, glibornuride or gliclazide.

In another embodiment, the compounds of the present invention are administered in combination with a biguamide such as, for example, metformin.

In another embodiment, the compounds of the present invention are administered in combination with a meglitinide such as, for example, repaglinide.

In yet another embodiment, the compounds of the present invention are administered in combination with a thiazolidinedione such as, for example, troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In yet another embodiment, the compounds of the present invention are administered in combination with a monoamine oxidase inhibitor such as disclosed, for example, in WO 01/12176. Particularly suitable for this purpose are [3(S),3a (S)]-3-methoxymethyl-7-[4,4,4-trifluorobutoxy]-3,3a,4,5-tetrahydro-1H-oxazolo[3,4-a]quinolin-1-one, (R)-5-(methoxymethyl)-3-[6-(4,4,4-trifluorobutoxy)benzofuran-3-yl]oxazolidin-2-one or (R)-5-(methoxymethyl)-3-[6-cyclopropylmethoxybenzofuran-3-yl]oxazolidin-2-one.

In another embodiment, the compounds of the present invention are administered in combination with an α-glucosidase inhibitor such as, for example, miglitol or acarbose.

In yet another embodiment, the present compounds are administered in combination with an hCNTF (human ciliary neurotrophic factor) or derivatives thereof, such as, for example, $CNTF_{AX15}$ or modified $CNTF_{AX15}$, such as disclosed, for example, in Lambert et al., PNAS 98, 4652–4657.

In another embodiment, the compounds of the present invention are administered in combination with an active compound which acts on the ATP-dependent potassium channel of the beta cells, such as, for example, tolbutamide, glibenclamide, glimepiride, glipizide, gliclazide or repaglinide.

In yet another embodiment, the compounds of the present invention are administered in combination with an antihyperlipidemic active compound or an antilipidemic active compound such as, for example, cholestyramine, colestipol, clofibrate, gemfibrozil, lovastatin, pravastatin, simvastatin, atorvastatin, cerivastatin, fluvastatin, probucol, ezetimibe or dextrothyroxine.

In another embodiment, the compounds of the present invention are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

Furthermore, the compounds of the invention may be administered in combination with one or more antiadipose agents or appetite-controlling active compounds.

Such active compounds may be selected from the group consisting of CART agonists, NPY antagonists, melanocortin 3 or 4 (MC3 or MC4) agonists, melanin-concentrating hormone (MCH) antagonists, orexin antagonists, H3 agonists, TNF agonists, CRF agonists, CRF BP antagonists, urocortin agonists, β3 adrenoceptor agonists, MSH (melanocyte-stimulating hormone) agonists, CCK agonists, serotonin re-uptake inhibitors, mixed serotonin and noradrenalin reuptake inhibitors, 5HT modulators, bombesin agonists, galanin antagonists, glucocorticoid receptor modulators, growth hormone, growth-hormone-releasing compounds, TRH agonists, uncoupling protein 2 or 3 modulators, leptin receptor agonists, leptin mimetics, dopamine agonists (bromocriptine, doprexin), lipase/amylase inhibitors, cannabinoid receptor 1 antagonists, modulators of acylation-stimulating protein (ASP), PPAR modulators, RXR modulators or TR-β agonists.

In one embodiment of the invention, the antiadipose agent is leptin or modified leptin.

In another embodiment, the antiadipose agent is dexamphetamine or amphetamine.

Such active compounds may be selected from the group consisting of CART agonists, NPY antagonists, melanocortin 3 or 4 (MC3 or MC4) agonists, melanin-concentrating hormone (MCH) antagonists, orexin antagonists, H3 agonists, TNF agonists, CRF agonists, CRF BP antagonists, urocortin agonists, β3 adrenoceptor agonists, CCK agonists, serotonin re-uptake inhibitors, mixed serotonin and noradrenalin reuptake inhibitors, 5HT modulators, bombesin agonists, galanin antagonists, glucocorticoid receptor modulators, growth hormone, growth-hormone-releasing compounds, TRH agonists, uncoupling protein 2 or 3 modulators, leptin receptor agonists, leptin mimetics, dopamine agonists (bromocriptine, doprexin), lipase/amylase inhibitors, cannabinoid receptor 1 antagonists, modulators of acylation-stimulating protein (ASP), PPAR modulators, RXR modulators or TR-β agonists.

In one embodiment of the invention, the antiadipose agent is leptin or modified leptin.

In another embodiment, the antiadipose agent is dexamphetamine or amphetamine.

In another embodiment, the antiadipose agent is fenfluramine or dexfenfluramine.

In yet another embodiment, the antiadipose agent is sibutramine or the mono- and bis-demethylated active metabolite of sibutramine.

In another embodiment, the antiadipose agent is orlistate.

In another embodiment, the antiadipose agent is mazindol, diethylpropione or phentermine.

Furthermore, the compounds of the present invention may be administered in combination with one or more antihypertensive active compounds. Examples of antihypertensive active compounds are betablockers such as alprenolol, atenol, timolol, pindolol, propanolol and metoprolol, ACE (angiotensin-converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and also alphablockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

It is self-evident that every suitable combination of the compounds of the invention with one or more of the aforementioned compounds and optionally one or more other pharmacologically active substances is to be regarded as covered by the scope of protection of the present invention.

The preparations below serve to illustrate the invention, without limiting it.

EXAMPLE A

Soft gelatin capsules, comprising 100 mg of active compound per capsule:

|  | per capsule |
| --- | --- |
| Active compound | 100 mg |
| Triglyceride mixture fractionated from coconut fat | 400 mg |
| Capsule contents | 500 mg |

EXAMPLE B

Emulsion, comprising 60 mg of active compound per 5 ml:

|  | per 100 ml of emulsion |
|---|---|
| Active compound | 1.2 g |
| Neutral oil | q.s. |
| Sodium carboxymethylcellulose | 0.6 g |
| Polyoxyethylene stearate | q.s. |
| Glycerol pure | 0.2 to 2.0 g |
| Flavoring | q.s. |
| Water (demineralized or distilled) | to 100 ml |

EXAMPLE C

Rectal administration form comprising 40 mg of active compound per suppository:

|  | per suppository |
|---|---|
| Active compound | 40 mg |
| Suppository base | ad 2 mg |

EXAMPLE D

Tablets comprising 40 mg of active compound per tablet:

|  | per tablet |
|---|---|
| Lactose | 600 mg |
| Corn starch | 300 mg |
| Soluble starch | 20 mg |
| Magnesium stearate | 40 mg |
|  | 1000 mg |

EXAMPLE E

Coated tablets comprising 50 mg of active compound per coated tablet:

|  | per coated tablet |
|---|---|
| Active compound | 50 mg |
| Corn starch | 100 mg |
| Lactose | 60 mg |
| Sec. calcium phosphate | 30 mg |

-continued

|  | per coated tablet |
|---|---|
| Soluble starch | 5 mg |
| Magnesium stearate | 10 mg |
| Colloidal silica | 5 mg |
|  | 260 mg |

EXAMPLE F

For preparing the contents of hard gelatin capsules, the following recipes are suitable:

| a) | Active compound | 100 mg |
|---|---|---|
|  | Corn starch | 300 mg |
|  |  | 400 mg |
| b) | Active compound | 140 mg |
|  | Lactose | 180 mg |
|  | Corn starch | 180 mg |
|  |  | 500 mg |

EXAMPLE G

Drops can be prepared according to the following recipe (100 mg of active compound in 1 ml=20 drops):

|  |  |
|---|---|
| Active compound | 10 g |
| Methyl benzoate | 0.07 g |
| Ethyl benzoate | 0.03 g |
| Ethanol 96% | 5 ml |
| Demineralized water | ad 100 ml |

The activity of the compounds of the formula I was assayed as follows:

Biological Test Model:

The anorectic action was tested on female NMRI mice. After removal of feed for 24 hours, the preparation to be tested was administered intraperitoneally (ip) or by gavage (po). The animals were housed singly and, with free access to drinking water, they were offered evaporated milk 30 minutes after administration of the preparation. The consumption of evaporated milk was determined and the general behavior of the animals was monitored every half an hour for 7 hours. The measured milk consumption was compared to that of vehicle-treated control animals.

TABLE 2

Anorectic action, measured as a reduction in the cumulative milk consumption by treated animals compared with control animals

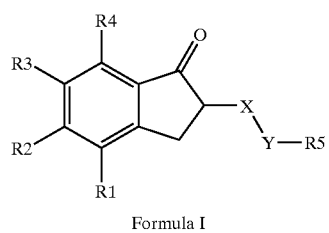

Formula I

|  | Dose [mg/kg] | Number of animals/ cumulative milk consumption by treated animals N/[ml] | Number of animals/ cumulative milk consumption by untreated control animals N/[ml] | Reduction in cumulative milk consumption as % of the contol |
|---|---|---|---|---|
| Example 1 | 10 (ip) | 05/1.20 | 05/3.30 | 64 |
| Example 2 | 20 (ip) | 05/1.16 | 05/3.86 | 70 |

TABLE 2-continued

Anorectic action, measured as a reduction in the cumulative milk consumption by treated animals compared with control animals

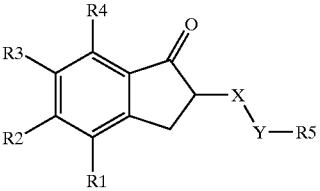

Formula I

| | Dose [mg/kg] | Number of animals/ cumulative milk consumption by treated animals N/[ml] | Number of animals/ cumulative milk consumption by untreated control animals N/[ml] | Reduction in cumulative milk consumption as % of the contol |
|---|---|---|---|---|
| Example 7 | 50 (po) | 05/1.76 | 05/5.52 | 68 |
| Example 9 | 50 (po) | 05/1.16 | 05/4.36 | 73 |

The table indicates that the compounds of the formula I exhibit very good anorectic action.

The preparation of some examples is described in detail below; the other compounds of the formula I were obtained analogously:

EXAMPLE 1

5–Chloro-2-methylsulfanylindan-1-one 0.98 g (4 mmol) of 2-bromo-5-chloroindan-1-one and 0.42 g (6 mmol) of sodium thiomethoxide were suspended in 5 ml of ethanol, treated in an ultrasonic bath for 30 minutes and then stirred at room temperature for 90 minutes. The reaction mixture was concentrated under reduced pressure and chromatographed on silica gel using toluene/ethyl acetate 10/1. The eluates were concentrated under reduced pressure, giving 0.63 g of 5-chloro-2-methylsulfanylindan-1-one of melting point 90° C.

EXAMPLE 2

5–Chloro-2-methanesulfonylindan-1-one 0.5 g of 5-chloro-2-methylsulfanylindan-1-one was dissolved in 10 ml of dry ethanol. At 0° C., a solution of 4.33 g of potassium hydrogenpersulfate ($2KHSO_5 \cdot xKHSO_4 \cdot xK_2SO_4$; "Oxone") in 10 ml of water was added dropwise and the reaction mixture was then stirred at room temperature for 5 h. The alcohol was distilled off under reduced pressure at room temperature. 20 ml of dichloromethane and 10 ml of water was added to the residue, and the mixture was stirred for 10 min. The organic phase was separated off, dried over magnesium sulfate, filtered and concentrated under reduced pressure, and the residue was dried. This gave 5-chloro-2-methylsulfonylindan-1-one of melting point 196° C.

EXAMPLE 3

5-chloro-2-phenylsulfanylindan-1-one 2.5 g of 2-bromo-5-chloroindan-1-one and 2.8 g of sodium thiophenoxide was suspended in 30 ml of ethanol and heated under reflux for 3 h. The cooled reaction mixture was concentrated and purified chromatographically on silica gel using toluene/ethyl acetate 10/1. This gave 5-chloro-2-phenylsulfanylindan-1-one of melting point 89° C.

EXAMPLE 4

2-benzenesulfonyl-5-chloroindan-1-one 1 g of 5-chloro-2-phenylsulfanylindan-1-one was oxidized as described in Example 2. This gave 2-benzenesulfonyl-5-chloroindan-1-one of melting point 133° C.

EXAMPLE 9

5-chloro-2-methanesulfinylindan-1-one

At room temperature, 4.5 g of sodium periodate were dissolved in 30 ml of water, the solution was cooled to 0° C. and a solution of 4.25 g of the compound of Example 1 in tetrahydrofuran (60 ml) was then added. The solution was stirred at room temperature overnight. The next day, the reaction mixture was diluted with ethyl acetate and water and the aqueous phase was separated off and extracted twice with ethyl acetate. The combined organic phases were washed with saturated sodium chloride solution, dried over magnesium sulfate, filtered and concentrated under reduced pressure. This gave 5-chloro-2-methanesulfinylindan-1-one of molecular weight 228 ($C_{10}H_9ClSO_2$); MS (ESI): 228.87 (MH$^+$).

The compounds of Examples 12–28, 31–33 and 36 were obtained as described in Example 1 by reacting the corresponding α-bromoindan-1-one with the sodium salt of the appropriate mercaptan.

The compounds of Examples 5–8, 10–11, 29, 30, 34 and 35 and 37–52 were obtained either by the method of Example 2 from the corresponding sulfanyl derivative or, in the case of methyl derivatives, by reacting the corresponding α-bromoindan-1-one with the sodium salt of methanesulfinic acid. Characterization was by HPLC/MS.

We claim:

1. A method of controlling weight in a mammal comprising administering to the mammal in need thereof at least one compound chosen from at least one compound of the formula (I)

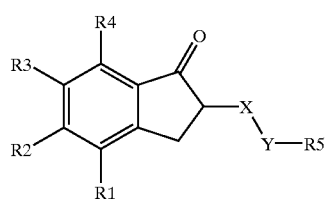

in which

R1, R2, R3, R4 independently of one another are H, F, Cl, Br, I, CN, $N_3$, $NO_2$, OH, O($C_1$–$C_8$)-alkyl, O($C_3$–$C_8$)-cycloalkyl, O—$CH_2$-phenyl, O-phenyl, O—CO—($C_1$–$C_8$)-alkyl, O—CO—($C_3$–$C_8$)-cycloalkyl, S(O)$_{0-2}$ ($C_1$–$C_8$)-alkyl, S(O)$_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)- alkyl, NH—CO—($C_3$–$C_8$)-cycloalkyl, $SO_3H$, $SO_2$—NH, $SO_2$—NH—($C_1$–$C_3$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)-cycloalkyl, ($C_2$–$C_8$)-alkenyl, or ($C_2$–$C_8$)-alkynyl, wherein the alkyl, cycloalkyl, alkenyl and alkynyl groups in each case have zero to seven hydrogen atoms replaced by fluorine, or one hydrogen may be replaced by OH, OC(O)$CH_3$, O—$CH_2$—Ph, $NH_2$, NH—CO—$CH_3$ or N(COOC$H_2$Ph)$_2$; or phenyl, 1- or 2-naphthyl, 5-tetrazolyl, 1-[($C_1$–$C_6$)-alkyl]-5-tetrazolyl, 2-[($C_1$–$C_6$)-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, 3-, 4- or 5-isothiazolyl, where the aryl radical or heterocycle is unsubstituted or substituted one to two times by F, Cl, Br, CN, OH, ($C_1$–$C_4$)-alkyl, $CF_3$, O—($C_1$–$C_4$)-alkyl, $S(O)_{0-2}$($C_1$–$C_6$)-alkyl, $NH_2$, NH—$SO_2$—($C_1$–$C_4$)-alkyl, COOH, CO—O—($C_1$–$C_4$)-alkyl, or CO—$NH_2$, wherein the alkyl groups in each case have zero to seven hydrogen atoms replaced by fluorine;

or R2 and R3 together form the group —O—$CH_2$—O—;

X is S, SO, or $SO_2$;

Y is $(CH_2)_p$, where p is 0, 1, 2 or 3;

R5 is $CF_3$, ($C_1$–$C_{18}$)-alkyl, ($C_3$–$C_8$)-cycloalkyl, wherein the alkyl or cycloalkyl groups in each case have zero to seven hydrogen atoms replaced by fluorine;

$(CH_2)_r$—COR6, where r is 1–6 and R6 is OH, O—($C_1$–$C_6$)-alkyl or $NH_2$;

$CH_2$—CH(NHR7)-COR8, where R7 is H, C(O)—($C_1$–$C_4$)-alkyl or C(O)O—($C_1$–$C_4$)-alkyl and R8 is OH, O—($C_1$–$C_6$)-alkyl or $NH_2$; or phenyl, 1- or 2-naphthyl, biphenyl or a heterocyclic radical, where the rings or ring systems are unsubstituted or substituted one or two times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl, $SO_3H$, $SO_2$—$NH_2$, $SO_2$—NH—($C_1$–$C_8$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, or ($C_3$–$C_8$)-cycloalkyl, where in the alkyl and cycloalkyl groups in each case have zero to seven hydrogen atoms replaced by fluorine, or F, Cl, Br, I, or CN;

or a physiologically tolerable salt thereof, in any stereoisomeric form, or a mixture of any such compounds in any ratio.

2. The method of claim 1, wherein

R1, R4 independently of one another are H, F, Cl, Br, I, CN, $N_3$, $NO_2$, OH, O($C_1$–$C_8$)-alkyl, O($C_3$–$C_4$ and $C_6$–$C_8$)-cycloalkyl, O—$CH_2$-phenyl, O-phenyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$, $SO_2$—$NH_2$, $SO_2$—NH—($C_1$–$C_8$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)-cycloalkyl, ($C_2$–$C_8$)-alkenyl, or ($C_2$–$C_8$)-alkynyl, where in the alkyl, cycloalkyl, alkenyl and alkynyl groups in each case have zero to seven hydrogen atoms replaced by fluorine, or one hydrogen may be replaced by OH, OC(O)$CH_3$, O—$CH_2$-Ph, $NH_2$, NH—CO—$CH_3$ or N(COOC$H_2$Ph)$_2$; or phenyl, 1- or 2-naphthyl, 5-tetrazolyl, 1-[($C_1$–$C_6$)-alkyl]-5-tetrazolyl, 2-[($C_1$–$C_6$)-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, or 3-, 4- or 5-isothiazolyl where the aryl radical or heterocycle are unsubstituted or substituted one or two times by F, Cl, Br, CN, OH, ($C_1$–$C_4$)-alkyl, $CF_3$, O—($C_1$–$C_4$)-alkyl, $S(O)_{0-2}$($C_1$–$C_6$)-alkyl, $NH_2$, NH—$SO_2$—($C_1$–$C_4$)-alkyl, COOH, CO—O—($C_1$–$C_4$)-alkyl, or CO—$NH_2$ wherein the alkyl groups in each case have zero to seven hydrogen atoms replaced by fluorine;

R2, R3 independently of one another are H, F, Cl, Br, I, CN, $N_3$, $NO_2$, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl, $SO_3H$, $SO_2$—$NH_2$, $SO_2$—NH—($C_5$–$C_8$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_5$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)-cycloalkyl, ($C_2$–$C_8$)-alkenyl, or ($C_2$–$C_8$)-alkynyl, where in the alkyl, cycloalkyl, alkenyl and alkynyl groups in each case have zero to seven hydrogen atoms replaced by fluorine, or one hydrogen may be replaced by OH, OC(O)$CH_3$, O—$CH_2$-Ph, $NH_2$, NH—CO—$CH_3$ or N(COOC$H_2$Ph)$_2$; or phenyl, 1-or 2-naphthyl, 5-tetrazolyl, 1-[($C_1$–$C_6$)-alkyl]-5-tetrazolyl,
2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl, or
3-, 4- or 5-isothiazolyl
where the heterocycle is unsubstituted or substituted one or two times by F, Cl, Br, CN, OH, ($C_1$–$C_4$)-alkyl, $CF_3$, O—($C_1$–$C_4$)-alkyl,
S(O)$_{0-2}$($C_1$–$C_6$)-alkyl, $NH_2$, NH—$SO_2$—($C_1$–$C_4$)-alkyl,
COOH, CO—O—($C_1$–$C_4$)-alkyl, or CO—$NH_2$ wherein the alkyl groups in each case have zero to seven hydrogen atoms replaced by fluorine;
or R2 and R3 together form the group —O—$CH_2$—O—;
where in each case at least one of the radicals R1, R2, R3 and R4 is different from hydrogen;
X is S, SO, or $SO_2$;
Y is $(CH_2)_p$, where p is 0, 1, 2 or 3;
R5 is ($C_1$–$C_{18}$)-alkyl, or ($C_3$–$C_4$— and $C_6$–$C_8$)-cycloalkyl, wherein the alkyl or cycloalkyl groups in each case have zero to seven hydrogen atoms replaced by fluorine;
$(CH_2)_r$—COR6, where r is 1–6 and R6 is OH, O—($C_1$–$C_6$)-alkyl or $NH_2$;
$CH_2$—CH(NHR7)-COR8, where R7 is H, C(O)—($C_1$–$C_4$)-alkyl or C(O)O—($C_1$–$C_4$)-alkyl and R8 is OH, O—($C_1$–$C_6$)-alkyl or $NH_2$;
phenyl, 1- or 2-naphthyl, biphenyl or a heterocyclic radical, where the rings or ring systems are unsubstituted or substituted up to two times by O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, S(O)$_{0-2}$($C_1$–$C_8$)-alkyl, S(O)$_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl $SO_3H$, $SO_2$—$NH_2$, $SO_2$—NH—($C_1$–$C_8$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, or ($C_3$–$C_8$)-cycloalkyl, where in the alkyl and cycloalkyl groups in each case have zero to seven hydrogen atoms replaced by fluorine; or
F, Cl, Br, I, or CN;
or a physiologically tolerable salt thereof, in any stereoisomeric form, or a mixture of any such compounds in any ratio.

3. The method of claim 1, wherein
R1, R4 independently of one another are H, F, Cl, or Br;
R2, R3 independently of one another are H, F, Cl, Br, CN, $CONH_2$, NH—$SO_2$—($C_1$–$C_8$)-alkyl, O—($C_1$–$C_8$)-alkyl, COOH, ($C_1$–$C_8$)-alkyl, ($C_1$–$C_8$)-alkenyl, or ($C_1$–$C_8$)-alkynyl, where in the alkyl, alkenyl and alkynyl groups in each case have zero to seven hydrogen atoms replaced by fluorine; or
phenyl, or 1-imidazolyl, where the rings are unsubstituted or substituted one or two times by F, Cl, Br, CN, OH, ($C_1$–$C_4$)-alkyl, or $CF_3$, O—($C_1$–$C_4$)-alkyl,
wherein the alkyl groups in each case have zero to seven hydrogen atoms may be replaced by fluorine;
where in each case at least one of the radicals R1, R2, R3 and R4 is different from hydrogen;
X is S or $SO_2$;
Y is $(CH_2)_p$, where p is 0 or 1;
R5 is ($C_1$–$C_{18}$)-alkyl or ($C_3$–$C_4$— and $C_6$–$C_8$)-cycloalkyl, wherein the alkyl or cycloalkyl groups have zero to seven hydrogen atoms replaced by fluorine;
$(CH_2)_r$—CO—O—($C_1$–$C_6$)-alkyl, where r is 1–6;
$CH_2$—CH(NHR7)-COR8, where R7 is H, C(O)—($C_1$–$C_4$)-alkyl or C(O)O—($C_1$–$C_4$)-alkyl and R8 is OH, O—($C_1$–$C_6$)-alkyl or $NH_2$;
phenyl, or a heterocyclic radical;
or a physiologically tolerable salt thereof, in any stereoisomeric form, or a mixture of any such compounds in any ratio.

4. The method of claim 1, wherein
R1 is H,
R2 is Cl,
R3 is H,
R4 is H,
R5 is $CH_3$,
X is S, and
Y is $(CH_2)_p$ where p is 0
or a physiologically tolerable salt thereof, in any stereoisomeric form, or a mixture of any such compounds in any ratio.

5. The method of claim 1, wherein
R1 is H,
R2 is Cl,
R3 is H,
R4 is H,
R5 is $CH_3$,
X is $SO_2$, and
Y is $(CH_2)_p$ where p is 0
or a physiologically tolerable salt thereof, in any stereoisomeric form, or a mixture of any such compounds in any ratio.

6. The method of claim 1, wherein
R1 is H,
R2 is HCC,
R3 is H,
R4 is H,
R5 is $CH_3$,
X is $SO_2$, and
Y is $(CH_2)_p$ where p is 0
or a physiologically tolerable salt thereof, in any stereoisomeric form, or a mixture of any such compounds in any ratio.

7. The method of claim 1, wherein
R1 is H,
R2 is Cl,
R3 is H,
R4 is H,
R5 is $CH_3$,
X is SO, and
Y is $(CH_2)_p$ where p is 0
or a physiologically tolerable salt thereof, in any stereoisomeric form, or a mixture of any such compounds in any ratio.

8. The method according to claim 1, wherein said at least one compound is administered in combination with at least one weight controlling active compound.

9. The method of claim 8, wherein said at least one weight controlling active compound is chosen from cathine, phenylpropanolamine, amfepramone, mefenorex, ephedrine, leptin, dexamphetamine, amphetamine, fenfluramine, dexfenfluramine, sibutramine, orlistat, mazindol or phentermine or salts thereof.

10. A method for the treatment of obesity in a mammal comprising administering to a mammal in need thereof at least one compound chosen from at least one compound of the formula (I)

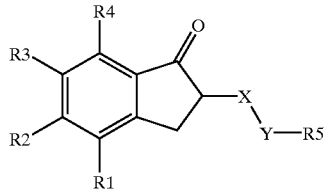

in which

R1, R2, R3, R4 independently of one another are H, F, Cl, Br, I, CN, $N_3$, $NO_2$, OH, $O(C_1-C_8)$-alkyl, $O(C_3-C_8)$-cycloalkyl, O—$CH_2$-phenyl, O-phenyl, O—CO—$(C_1-C_8)$-alkyl, O—CO—$(C_3-C_8)$-cycloalkyl, $S(O)_{0-2}$$(C_1-C_8)$-alkyl, $S(O)_{0-2}$$(C_3-C_8)$-cycloalkyl, $NH_2$, NH—$(C_1-C_8)$-alkyl, NH—$(C_3-C_8)$-cycloalkyl, $N[(C_1-C_8)$-alkyl$]_2$, $N[(C_3-C_8)$-cycloalkyl$]_2$, NH—CO—$(C_1-C_8)$-alkyl, NH—CO—$(C_3-C_8)$-cycloalkyl, $SO_3H$, $SO_2$—$NH_2$, $SO_2$—NH—$(C_1-C_8)$-alkyl, $SO_2$—NH—$(C_3-C_8)$-cycloalkyl, NH—$SO_2$—$NH_2$, NH—$SO_2$—$(C_1-C_8)$-alkyl, NH—$SO_2$—$(C_3-C_8)$-cycloalkyl, O—$CH_2$—COOH, O—$CH_2$—CO—$O(C_1-C_3)$-alkyl, O—$CH_2$—COOH, O—$CH_2$—CO—$O(C_1-C_8)$-alkyl, COOH, CO—$O(C_1-C_8)$-alkyl, CO—O—$(C_3-C_8)$-cycloalkyl, CO—$NH_2$, CO—NH$(C_1-C_8)$-alkyl, CO—N$[(C_1-C_8)$-alkyl$]_2$, $(C_1-C_8)$-alkyl, $(C_3-C_8)$-cycloalkyl, $(C_2-C_8)$-alkenyl, or $(C_2-C_8)$-alkynyl, wherein the alkyl, cycloalkyl, alkenyl and alkynyl groups in each case have zero to seven hydrogen atoms replaced by fluorine, or one hydrogen may be replaced by OH, $OC(O)CH_3$, O—$CH_2$-Ph, $NH_2$, NH—CO—$CH_3$ or $N(COOCH_2Ph)_2$; or phenyl, 1- or 2-naphthyl,
5-tetrazolyl, 1-$[(C_1-C_6)$-alkyl]-5-tetrazolyl, 2-$[(C_1-C_6)$-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl,
3-, 4- or 5-isothiazolyl,
where the aryl radical or heterocycle is unsubstituted or substituted one to two times by F, Cl, Br, CN, OH, $(C_1-C_4)$-alkyl, $CF_3$, O—$(C_1-C_4)$-alkyl, $S(O)_{0-2}$$(C_1-C_6)$-alkyl, $NH_2$, NH—$SO_2$—$(C_1-C_4)$-alkyl, COOH, CO—O—$(C_1-C_4)$-alkyl, or CO—$NH_2$, wherein the alkyl groups in each case have zero to seven hydrogen atoms replaced by fluorine;
or R2 and R3 together form the group —O—$CH_2$—O—;
X is S, SO, or $SO_2$;
Y is $(CH_2)_p$, where p is 0, 1, 2 or 3;

R5 is $CF_3$, $(C_1-C_{18})$-alkyl, $(C_3-C_8)$-cycloalkyl, wherein the alkyl or cycloalkyl groups in each case have zero to seven hydrogen atoms replaced by fluorine;
$(CH_2)_r$—COR6, where r is 1–6 and R6 is OH, O—$(C_1-C_6)$-alkyl or $NH_2$;
$CH_2$—CH(NHR7)-COR8, where R7 is H, C(O)—$(C_1-C_4)$-alkyl or $C(O)O$—$(C_1-C_4)$-alkyl and R8 is OH, O—$(C_1-C_6)$-alkyl or $NH_2$; or
phenyl, 1- or 2-naphthyl, biphenyl or a heterocyclic radical, where the rings or ring systems are unsubstituted or substituted one or two times by F, Cl, Br, I, CN, OH, $O(C_1-C_8)$-alkyl, $O(C_3-C_8)$-cycloalkyl, O—CO—$(C_1-C_8)$-alkyl, O—CO—$(C_3-C_8)$-cycloalkyl, $S(O)_{0-2}$$(C_1-C_8)$-alkyl, $S(O)_{0-2}$$(C_3-C_8)$-cycloalkyl, $NH_2$, NH—$(C_1-C_8)$-alkyl, NH—$(C_3-C_8)$-cycloalkyl, $N[(C_1-C_8)$-alkyl$]_2$, $N[(C_3-C_8)$-cycloalkyl$]_2$, NH—CO—$(C_2-C_8)$-alkyl, NH—CO—$(C_3-C_8)$-cycloalkyl, $SO_3H$, $SO_2$—$NH_2$, $SO_2$—NH—$(C_1-C_8)$-alkyl, $SO_2$—NH—$(C_3-C_8)$-cycloalkyl, NH—$SO_2$—$NH_2$, NH—$SO_2$—$(C_1-C_8)$-alkyl, NH—$SO_2$—$(C_3-C_8)$-cycloalkyl, O—$CH_2$—COOH, O—$CH_2$—CO—$O(C_1-C_8)$-alkyl, COOH, CO—$O(C_1-C_8)$-alkyl, CO—O—$(C_3-C_8)$-cycloalkyl, CO—$NH_2$, CO—NH$(C_1-C_8)$-alkyl, CO—N$[(C_1-C_8)$-alkyl$]_2$, $(C_1-C_8)$-alkyl, or $(C_3-C_8)$-cycloalklyl, where in the alkyl and cycloalkyl groups in each case have zero to seven hydrogen atoms replaced by fluorine, or
F, Cl, Br, I, or CN;

or a physiologically tolerable salt thereof, in any stereoisomeric form, or a mixture of any such compounds in any ratio.

11. The method of claim 10, wherein
R1 is H,
R2 is Cl,
R3 is H,
R4 is H,
R5 is $CH_3$,
X is S, and
Y is $(CH_2)_p$ where p is 0
or a physiologically tolerable salt thereof, in any stereoisomeric form, or a mixture of any such compounds in any ratio.

12. The method of claim 10, wherein
R1 is H,
R2 is Cl,
R3 is H,
R4 is H,
R5 is $CH_3$,
X is $SO_2$, and
Y is $(CH_2)_p$ where p is 0
or a physiologically tolerable salt thereof, in any stereoisomeric form, or a mixture of any such compounds in any ratio.

13. The method of claim 10, wherein
R1 is H,
R2 is HCC,
R3 is H,
R4 is H,
R5 is $CH_3$,
X is $SO_2$, and
Y is $(CH_2)_p$ where p is 0
or a physiologically tolerable salt thereof, in any stereoisomeric form, or a mixture of any such compounds in any ratio.

14. The method of claim 10, wherein
R1 is H,
R2 is Cl,
R3 is H,
R4 is H,
R5 is $CH_3$,
X is SO, and
Y is $(CH_2)_p$ where p is 0
or a physiologically tolerable salt thereof, in any stereoisomeric form, or a mixture of any such compounds in any ratio.

15. The method according to claim 10, wherein said at least one compound is administered in combination with at least one weight controlling active compound.

16. The method of claim 15, wherein said at least one weight controlling active compound is chosen from cathine, phenylpropanolamine, amfepramone, mefenorex, ephedrine, leptin, dexamphetamine, amphetamine, fenfluramine, dexfenfluramine, sibutramine, orlistat, mazindol or phentermine or salts thereof.

* * * * *